United States Patent
Schomaker et al.

(10) Patent No.: US 10,233,162 B2
(45) Date of Patent: Mar. 19, 2019

(54) ELECTRONICALLY ACTIVATED STRAINED ALKYNES

(71) Applicant: Wisconsin Alumni Research Foundation, Madison, WI (US)

(72) Inventors: Jennifer M. Schomaker, Madison, WI (US); Eileen G. Burke, Somerville, MA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/873,984

(22) Filed: Jan. 18, 2018

(65) Prior Publication Data

US 2018/0201593 A1   Jul. 19, 2018

Related U.S. Application Data

(60) Provisional application No. 62/447,466, filed on Jan. 18, 2017.

(51) Int. Cl.
  *C07D 291/02* (2006.01)
  *C07D 285/08* (2006.01)
  *C07D 285/38* (2006.01)

(52) U.S. Cl.
  CPC ......... *C07D 291/02* (2013.01); *C07D 285/38* (2013.01)

(58) Field of Classification Search
  CPC ........................... C07D 285/08; C07D 291/02
  See application file for complete search history.

(56) References Cited

PUBLICATIONS

Burke. Journal of the American Chemical Society, 2017, 139, 8029-37, published May 15, 2017 (Year: 2017).*
Baskin, J. M.; Bertozzi, C. R. (2007) "Bioorthogonal Click Chemistry: Covalent Labeling in Living Systems," *QSAR Comb. Sci.* 26:1211-1219.
Castro, Rodríguez and Albericio (2016) "CuAAC: An Efficient Click Chemistry Reaction on Solid Phase," *ACS Comb. Sci.* 18(1):1-14.
Codelli, J. A.; Baskin, J. M.; Agard, N. J.; Bertozzi, C. R. (2008) "Second-Generation Difluorinated Cyclooctynes for Copper-Free Click Chemistry," *J. Am. Chem. Soc.* 130:11486-11493.
Evans, R. A. (2007) "The Rise of Azide-Alkyne 1,3-Dipolar 'Click' Cycloaddition and its Application to Polymer Science and Surface Modification," *Australian Journal of Chemistry* 60(6): 384-395.

Greene's Protective Groups in Organic Synthesis, ISBN-13: 978-1118057483, ©2014, John Wiley & Sons, Inc. (In particular, see Chapter 1, Protecting Groups: An Overview, Chapter 2, Hydroxyl Protecting Groups,Chapter 4, Carboxyl Protecting Groups, and Chapter 5, Carbonyl Protecting Groups).
Handbook of Pharmaceutical Salts: Properties, Selection, and Use, 2nd Revised Edition, P.H. Stahl and C.G. Wermuch, Eds., © 2011 Wiley-VCH, an imprint of John Wiley & Sons, Inc. (Hoboken, New Jersey), ISBN 978-3-90639-051-2.
Hoyle, Charles E.; Bowman, Christopher N. (2010) "Thiol-Ene Click Chemistry," *Angewandte Chemie International Edition* 49(9):1540-1573.
Johnson, J. A.; Baskin, J. M.; Bertozzi, C. R.; Koberstein, J. T.; Turro, N. J. (2008) "Copper-free click chemistry for the in situ crosslinking of photodegradable star polymers," *Chem. Commun.* 3064-3066.
Kocienski, Philip J. "Protecting Groups," (Georg Thieme Verlag Stuttgart, New York, 1994).
Kolb, H. C.; Finn, M. G.; Sharpless, K.B. (2001) "Click Chemistry: Diverse Chemical Function from a Few Good Reactions," *Angewandte Chemie International Edition* 40(11): 2004-2021.
Ni, Mitsuda, Kashiwagi, Igawa, and Tomooka (2015) "Heteroatom-embedded Medium-Sized Cycloalkynes: Concise Synthesis, Structural Analysis, and Reactions," *Angewandte Chemie International* 54(4): 1190-1194.
Sletten, E. M.; Bertozzi, C. R. (2008) "A Hydrophilic Azacyclooctyne for Cu-Free Click Chemistry," *Org. Lett.* 10:3097-3099.
Spiteri, Christian; Moses, John E. (2010) "Copper-Catalyzed Azide-Alkyne Cycloaddition: Regioselective Synthesis of 1,4,5-Trisubstituted 1,2,3-Triazoles," *Angewandte Chemie International Edition* 49(1):31-33.

\* cited by examiner

*Primary Examiner* — Noble E Jarrell
(74) *Attorney, Agent, or Firm* — Joseph T. Leone, Esq.; DeWitt LLP (57) ABSTRACT

Compounds of Formula I:

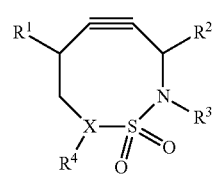

(Formula I)

wherein:
R$^1$ and R$^2$ are hydrogen or C$_1$ to C$_{12}$ linear or branched alkyl; R$^3$ is hydrogen, C$_1$ to C$_{12}$ linear or branched alkyl, or nitrogen protecting groups; X is oxygen or nitrogen; and when X is oxygen, R$^4$ is absent; and when X is nitrogen, R$^4$ is C$_1$ to C$_{12}$ linear or branched alkyl or nitrogen protecting groups. The compounds are useful as reagents in 1,3-cycloaddition reactions.

26 Claims, 5 Drawing Sheets

*Previous work: electronic effects on azide–alkyne cycloadditions*

A

Bertozzi (2007)
~30-fold rate increase

$k_2 = 0.002$      $k_2 = 0.076$

B

Alabugin (2012)
stereoelectronic interactions
increase reactivity;
computational optimization $\Delta E^\ddagger_{calc.}$ = 9.8 kcal/mol    8.5 kcal/mol

C

Tomooka (2015)
synthesis and reactivity
of various cyclononynes
and a thia-aza-cyclooctyne $k_2 = 0.019$      $k_2 = 0.009$

*This work:*

D

– unexpectedly large effect of a single propargylic heteroatom
– increased effects in cycloadditions of diazoacetamides over azides
– ease of synthesis and manipulation

ELECTRONICALLY ACTIVATED STRAINED ALKYNES

CROSS-REFERENCE TO RELATED APPLICATIONS

Priority is hereby claimed to provisional application Ser. No. 62/447,466, filed 18 Jan. 2017, which is incorporated herein by reference.

FEDERAL FUNDING STATEMENT

This invention was made with government support under GM 111412 awarded by the National Institutes of Health. The government has certain rights in the invention.

BACKGROUND

The difficulty of synthesizing a diverse array of complex molecules from readily available precursors has led to the development of many elegant and highly specific transformations in efforts to reach desired targets. An alternate approach to generating many specialized transformations focuses instead on using a small pool of highly efficient reactions. The idea of "click chemistry" mimics nature's modular usage of heteroatom linkages to afford a wide variety of macromolecular scaffolds. See H. C. Kolb; M. G. Finn; K. B. Sharpless (2001) "Click Chemistry: Diverse Chemical Function from a Few Good Reactions," *Angewandte Chemie International Edition* 40(11):2004-2021. While it is unlikely this approach would completely supplant the traditional strategies of molecular synthesis, the use of "click chemistry" has had notable applications and widespread use. See, for example, R. A. Evans (2007) "The Rise of Azide-Alkyne 1,3-Dipolar 'Click' Cycloaddition and its Application to Polymer Science and Surface Modification," *Australian Journal of Chemistry* 60(6):384-395; Spiteri, Christian; Moses, John E. (2010) "Copper-Catalyzed Azide-Alkyne Cycloaddition: Regioselective Synthesis of 1,4,5-Trisubstituted 1,2,3-Triazoles," *Angewandte Chemie International Edition* 49(1):31-33; and Hoyle, Charles E.; Bowman, Christopher N. (2010) "Thiol-Ene Click Chemistry," *Angewandte Chemie International Edition* 49(9):1540-1573.

In the design and optimization of reactions used in this manner, basic principles of chemical reactivity must be utilized. Whether a cascade reaction leads to a complex natural product (for example, a specialized Diels-Alder cycloadditions employed by Boger) or a simple $S_N2$ displacement, understanding how to manipulate weak bonds in starting compounds and transform them into strong bonds in the products requires the presence of a "driving force." When the inherent energy profile is not favorable for the desired reaction to go to completion, an extra 'push' is often provided by a catalyst. This is the case for arguably the most efficient "click" reaction, the copper-catalyzed azide-alkyne cycloaddition (CuAAC). See, for example, Castro, Rodríguez and Albericio (2016) "CuAAC: An Efficient Click Chemistry Reaction on Solid Phase," *ACS Comb. Sci.* 18(1):1-14. While CuAAC is undoubtedly an incredibly valuable transformation with broad applications, limitations do exist which are often linked to the requirement for this catalyst.

In place of a catalyst, one highly effective strategy to promote reactivity has been the use of the release of strain energy. See FIG. 1, panels A, B, and C. However, incorporating strained alkynes into the starting compounds can increase reactivity of the alkyne bond to the point that is extremely difficult to isolate the starting compound. In fact, early attempts required a cycloaddition reaction to trap the intermediate cyclooctynes in order to prove their generation in situ. Since these early reports of strain as a method to increase reactivity, there has been intense interest in these unique molecules that was further renewed when strain was applied to azide-alkyne cycloadditions (strain-promoted azide-alkyne cycloadditions, SPAAC). See, for example, Baskin, J. M.; Bertozzi, C. R. (2007) "Bioorthogonal Click Chemistry: Covalent Labeling in Living Systems," *QSAR Comb. Sci.* 26:1211-1219; Codelli, J. A.; Baskin, J. M.; Agard, N. J.; Bertozzi, C. R. (2008) "Second-Generation Difluorinated Cyclooctynes for Copper-Free Click Chemistry," *J. Am. Chem. Soc.* 130:11486-11493; Johnson, J. A.; Baskin, J. M.; Bertozzi, C. R.; Koberstein, J. T.; Turro, N. J. (2008) "Copper-free click chemistry for the in situ cross-linking of photodegradable star polymers," *Chem. Commun.* 3064-3066; and Sletten, E. M.; Bertozzi, C. R. (2008) "A Hydrophilic Azacyclooctyne for Cu-Free Click Chemistry," *Org. Lett.* 10:3097-3099.

The strain energy present in various cycloalkynes was used by Bertozzi and co-workers, supra, to sidestep the cytotoxicity associated with CuAAC by eliminating the need for copper catalysts, which proved problematic when attempting to use Huisgen 1,3-dipolar reactions in vivo. Since this initial report, new cyclic alkynes have been reported, with properties expanding the utility of this chemistry. These types of reactions are used in various fields, including biological labeling, the synthesis of specialized polymers and ligands, and the generation of libraries of medicinally relevant compounds.

The value of cycloalkynes is due, in part, to their fast rates of reaction. As a result, several strategies have been explored to increase their reactivity in a predictable and controllable manner. The most common approach involves "ring strain activation," where cyclopropanes, aryl groups or other sites of unsaturation are introduced into the molecule providing for rate enhancement of >2 orders of magnitude. Examples include the compounds known by their trivial names as bicyclo[6.1.0]nonyne ("BCN"), dibenzocyclooctynone ("DIBONE"), and dibenzoazacyclooctyne ("DIBAC"):

However, this strategy can be problematic, as these changes result in inherent destabilization of the ring. Cycloalkynes activated primarily by increased strain may become sensitive to heat or light, they require harsh conditions to prepare, and typically have a very short shelf life.

A different tactic to increase reactivity is achieved by manipulation of the desired reaction's transition state through electronic stabilization, in addition to the typical ring strain. See FIG. 1, panels A and B. This allows for an increase in reactivity over alkynes which rely solely on strain activation without sacrificing stability of the alkyne. In addition to raising the reactivity of the alkyne, combining electronic activation with strain offers the possibility of tuning each alkyne to a distinct coupling partner. Theoretically, this should yield alkynes with both fast reaction rates and selective reactivity.

The most successful previous efforts to combine strain and electronic effects take advantage of the increased reactivity provided by electronegative atoms at the propargylic position. Again, see FIG. 1 at panels A and B. It has been shown that rate enhancements which stem from hyperconjugative $\pi \to \sigma^*_{C-X}$ interactions are especially important contributors in the transition state (TS). When σ-acceptors are also contained within the cyclic framework, they allow for strengthened hyper-conjugative ($\pi \to \sigma^*_{C-X}$) interactions relative to systems containing exocyclic σ-acceptors. This is a result of the orientation of the endocyclic propargylic atom(s), which lie antiperiplanar relative to the new bonds being formed. See FIG. 1, panel B. When the σ-acceptor is located in an endocyclic orientation, it is already positioned appropriately for maximal electronic interaction in the transition state. This is in contrast to the gauche orientation noted when the propargylic σ-acceptors are exocyclic, as the propargylic C—C bond of the ring precludes them from adopting the ideal antiperiplanar geometry. Tomooka and co-workers recently synthesized medium-sized cycloalkynes with heteroatoms embedded at the propargylic positions that enable cycloaddition rates faster than those of cyclooctyne ("OCT") and monofluorinated cyclooctyne ("MOFO"), but do not yet surpass those of difluorocyclooctyne (DIFO). See Ni, Mitsuda, Kashiwagi, Igawa, and Tomooka (2015) "Heteroatom-embedded Medium-Sized Cycloalkynes: Concise Synthesis, Structural Analysis, and Reactions," *Angewandte Chemie International* 54(4):1190-1194.

Although many impressive strained alkynes have been reported, the existing chemistry remains far from optimal. There is an ongoing and unmet need for new strained cycloalkynes that offer ease and flexibility in synthesis, chemoselectivity, and reduced lipophilicity.

SUMMARY

Disclosed herein is a new class of cycloalkynes which incorporate heteroatoms into the ring. Also disclosed are method to make these novel cycloalkynes, and their use as reactants in 1,3-dipolar cycloaddition reactions. This method to make the cycloalkynes is very flexible and can be used to make a host of modifications to the basic structure. The resulting cycloalkynes are thus "tunable" with respect to their rate of reaction and their chemoselectivity against both unwanted side reactions and the potential for selective reactivity between different types of dipoles (for example, selective reactivity with azide dipoles versus diazoacetamide dipoles).

Disclosed are compounds of Formula I:

(Formula I)

wherein:
$R^1$ and $R^2$ are independently selected from hydrogen and $C_1$ to $C_{12}$ linear or branched alkyl;
$R^3$ is selected from hydrogen, $C_1$ to $C_{12}$ linear or branched alkyl, and nitrogen protecting groups;
X is oxygen or nitrogen;
when X is oxygen, $R^4$ is absent; and
when X is nitrogen, $R^4$ is selected from $C_1$ to $C_{12}$ linear or branched alkyl and nitrogen protecting groups.

Also disclosed herein is a method of forming chemical bonds. The method comprises reacting a first compound as recited in the preceding paragraph with a second compound comprising a 1,3-dipole in a 1,3-cycloaddition reaction.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. The indefinite article "a," when applied to a claimed element, means "one or more," unless explicitly stated to the contrary.

All combinations of method or process steps as used herein can be performed in any order, unless otherwise specified or clearly implied to the contrary by the context in which the referenced combination is made.

The methods, compounds, and compositions of the present invention can comprise, consist of, or consist essentially of the essential elements and limitations of the invention as described herein, as well as any additional or optional ingredients, components, or limitations described herein or otherwise useful in synthetic organic chemistry.

DETAILED DESCRIPTION

Abbreviations and Definitions

BCN=bicyclo[6.1.0]nonyne.
CuAAC=copper-catalyzed azide-alkyne cycloaddition.
DIBAC=dibenzoazacyclooctyne.
DIBONE=dibenzocyclooctynone.
IEFPCM=integral equation formalism variant of the polarizable continuum model.
NBO=natural bond orbital.
OCT=cyclooctyne
SPAAC=strain-promoted alkyne-azide cyclization.
TBAF=tetra-n-butylammonium fluoride
TS=transition state.
UFF=universal force field.

In the present description, unless otherwise indicated, terms such as "compounds of the invention" and "compounds disclosed herein" embrace the compounds in salt form as well as in free acid or base form (as the case may be) and also when the compounds are attached to a solid phase. Where a basic substituent such as an amine substituent is present, the salt form may be an acid addition salt, for example a dihydrochloride. Conversely, where an acidic substituent is present, the salt form may be a base addition salt. Salts include, without limitation, acid addition salts such as those derived from mineral acids and organic acids, explicitly including hydrohalides, e.g., hydrochlorides and hydrobromides, sulfates, phosphates, nitrates, sulfamates, acetates, citrates, lactates, tartrates, malonates, oxalates, salicylates, propionates, succinates, fumarates, maleates, methylene bis-b-hydroxynaphthoates, gentisates, isethionates, di-p-toluoyltartrates, methane sulfonates, ethanesulfonates, benzenesulfonates, p-toluenesulfonates, cyclohexylsulfamates, quinates, and the like. Base addition salts include those derived from alkali or alkaline earth metal bases or conventional organic bases, such as triethylamine, pyridine, piperidine, morpholine, N-methylmorpholine, and the like. Other suitable salts are found in, for example, "Handbook of Pharmaceutical Salts: Properties, Selection, and Use, $2^{nd}$ Revised Edition," P. H. Stahl and C. G. Wermuch, Eds., © 2011 Wiley-VCH, an imprint of John Wiley & Sons, Inc. (Hoboken, N.J.), ISBN 978-3-90639-051-2, which is incorporated herein by reference.

The invention includes the compounds of the invention in pure isomeric form, e.g., consisting of at least 90%, preferably at least 95% of a single isomeric form, as well as mixtures of these forms. The compounds of the invention may also be in the form of individual enantiomers or may be in the form of racemates or diastereoisomeric mixtures or any other mixture of the possible isomers.

A "protecting group" is any chemical moiety capable of selective addition to and removal from a reactive site to allow manipulation of a chemical entity at sites other than the reactive site. Many protecting groups are known in the art. A large number of protecting groups and corresponding chemical cleavage reactions are described in "Greene's Protective Groups in Organic Synthesis," ISBN-13: 978-1118057483, ©2014, John Wiley & Sons, Inc. The term "nitrogen protecting group" is specifically directed to protecting groups that are capable of selective addition to and removal from a reactive nitrogen atom in a molecule (to allow manipulation of a chemical entity at sites other than the protected, reactive nitrogen atom). Greene describes many nitrogen protecting groups, for example, amide-forming groups. In particular, see Chapter 1, Protecting Groups: An Overview, Chapter 2, Hydroxyl Protecting Groups, Chapter 4, Carboxyl Protecting Groups, and Chapter 5, Carbonyl Protecting Groups. For additional information on protecting groups, see also Kocienski, Philip J. "Protecting Groups," (Georg Thieme Verlag Stuttgart, New York, 1994), which is incorporated herein by reference. Typical nitrogen protecting groups described in Greene include benzyl ethers, silyl ethers, esters including sulfonic acid esters, carbonates, sulfates, and sulfonates. For example, suitable nitrogen protecting groups include substituted methyl ethers; substituted ethyl ethers; p-chlorophenyl, p-methoxyphenyl, 2,4-dinitrophenyl, benzyl; substituted benzyl ethers (p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, diphenylmethyl, 5-dibenzosuberyl, triphenylmethyl, p-methoxyphenyl-diphenylmethyl, di(p-methoxyphenyl)phenylmethyl, tri(p-methoxyphenyl)methyl, 1,3-benzodithiolan-2-yl, benzisothiazolyl S,S-dioxido); silyl ethers (silyloxy groups) (trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxy-phenylsilyl); esters (formate, benzoylformate, acetate, choroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), pivaloate, adamantoate, crotonate, 4-methoxycrotonate, benzoate, p-phenylbenzoate, 2,4,6-trimethylbenzoate(mesitoate)); carbonates (methyl, 9-fluorenylmethyl, ethyl, 2,2,2-trichloroethyl, 2-(trimethylsilyl) ethyl, 2-(phenylsulfonyl)ethyl, 2-(triphenylphosphonio) ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate); groups with assisted cleavage (2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, miscellaneous esters (2,6-dichloro-4-methylphenoxyacetate, 2,6-dichloro-4-(1,1,3,3 tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate (tigloate), o-(methoxycarbonyl)benzoate, p-poly-benzoate, α-naphthoate, nitrate, alkyl N,N,N',N'-tetramethyl-phosphorodiamidate, n-phenylcarbamate, borate, 2,4-dinitrophenylsulfenate); or sulfonates (methanesulfonate(mesylate), benzenesulfonate, benzylsulfonate, tosylate, or triflate).

The more common of the amine-protecting groups have trivial abbreviations that are widely used in the literature and include: carbobenzyloxy (Cbz) group (removed by hydrogenolysis), p-methoxybenzyl carbonyl (Moz or MeOZ) group (removed by hydrogenolysis), tert-butyloxycarbonyl (BOC) group (common in solid phase peptide synthesis; removed by concentrated strong acid (such as HCl or $CF_3COOH$), or by heating to >80° C., 9-fluorenylmethyloxycarbonyl (FMOC) group (also common in solid phase peptide synthesis; removed by base, such as piperidine), acetyl (Ac) group (removed by treatment with a base), benzoyl (Bz) group (removed by treatment with a base), benzyl (Bn) group (removed by hydrogenolysis), carbamate group (removed by acid and mild heating), p-methoxybenzyl (PMB) (removed by hydrogenolysis), 3,4-dimethoxybenzyl (DMPM) (removed by hydrogenolysis), p-methoxyphenyl (PMP) group (removed by ammonium cerium(IV) nitrate (CAN)), tosyl (Ts) group (removed by concentrated acid and strong reducing agents), sulfonamide groups (Nosyl & Nps; removed by samarium iodide, tributyltin hydride.

As used herein, the phrase "1,3-dipole," as in "a compound comprising a 1,3-dipole", means dipolar compounds having delocalized electrons and a separation of charge over three atoms and capable of being a reactant in a 1,3-dipolar cycloaddition reaction. A non-exclusive list of compounds comprising a 1,3-dipole includes azides (R—$N_3$), ozone ($O_3$), nitro compounds (R—$NO_2$), diazo compounds ($R_2$—C=N=N), certain oxides (such as, but not limited to azoxide compounds (RN(O)NR) carbonyl oxides (Criegee zwitterions), nitrile oxides (RCN—O), nitrous oxide ($N_2O$), and nitrones ($R_2CN(R)O$), carboynyl oxide, certain imines (such as azomethine imine, nitrilimines (RCN—NR, analogous to nitrile oxide) and carbonyl imines), and certain ylides (including azomethine ylide, nitrile ylide (RCNCR'$_2$), carbonyl ylide, and thiosulfines ($R_2CSS$)).

1,3-dipoles may also be organized by structure as nitrogen-centered or oxygen-centered allyl-type or propargyl-allenyl-type. Nitrogen-centered, allyl-type 1,3-dipoles include, but are not limited to:

Oxygen-centered, allyl-type 1,3-dipoles include, but are not limited to:

Propargyl-allenyl-type 1,3-dipoles include, but are not limited to, nitrilium betaines such as as well as diazonium betaines, such as Synthesis of Strained Cycloalkynes:

One of the ongoing challenges when using conventional strained cycloalkynes is their very difficult synthesis. Prior art syntheses are lengthy and offer few opportunities for derivatization. In contrast, the present process begins with readily accessible silylated allenes (1, Scheme 1). The presence of the silyl group directs the regioselectivity of the aziridination to the distal allene to yield an endocyclic methylene aziridine 2. In prior art syntheses, the remaining alkene underwent diastereoselective epoxidation, followed by rapid rearrangement, to form azetidin-3-ones represented by 3. However, the inventive process treats 2 with TBAF, which triggers elimination of the silyl group, followed by ring-opening of the aziridine, to yield the novel strained alkyne 4 with heteroatoms incorporated into the ring at strategic positions.

The scope of the reaction is illustrated in Table 1. Analogs of the allenic precursor 1 allow for varied alkyl substitution at the C1 and C4 positions. This allowed for an investigation of the effects of steric bulk, as well as a demonstration of the ability to include tethered functional groups. The propargyl nitrogen can be protected, which permits the electronic properties and strain experienced by the alkyne to be varied or "tuned." Additionally, the homopropargylic oxygen atom can be replaced with a nitrogen atom by using a homoallenic sulfamide precursor. The flexibility of this scaffold allows for tuning of the strained alkyne. The synthetic approach can also be used to optimize the reactivity of the alkyne for its desired coupling partner (vide infra). Overall, the synthesis is rapid, high yielding, and easily diversified. It is also notable that these strained alkynes are easily isolable solids which are stable to heat and light, as well as to both acidic and basic reaction conditions. The stability of the inventive cyclooctynes in the presence of biologically relevant functional groups, including a free thiol, was assessed by stirring the alkyne with glutathione in a PBS buffered solution for 24 h. No reaction was observed.

TABLE 1

Scope of cycloalkyne formation and reactivity with benzyl azide.

| entry | substrate | product | yield (%) | 1,3-dipolar cycloaddition | | |
|---|---|---|---|---|---|---|
| | | | | yield (%) | $k_2$ | $k_{rel.}$ |
| 1 | 1a | 4a | XX | XX | 0.066 | 2.6 |
| 2 | 1b | 4b | XX | XX | 0.025 | 1.0 |
| 3 | 1c | 4c | XX | XX | 0.0040 | 0.16 |

TABLE 1-continued

Scope of cycloalkyne formation and reactivity with benzyl azide.

| entry | substrate | product | yield (%) | 1,3-dipolar cycloaddition yield (%) | $k_2$ | $k_{rel.}$ |
|---|---|---|---|---|---|---|
| 4 | 1d | 4d | XX | XX | 0.037 | 1.5 |
| 5 | 1e | 4e | XX | XX | 0.042 | 1.7 |
| 6 | 1f | 4f | XX | XX | XX | XX |

TABLE 1-continued

Scope of cycloalkyne formation and reactivity with benzyl azide.

| entry | substrate | product | yield (%) | 1,3-dipolar cycloaddition yield (%) | $k_2$ | $k_{rel.}$ |
|---|---|---|---|---|---|---|
| 7 | 1g | 4g | XX | XX | 0.047 | 1.9 |
| 8 | 1h | 4h | XX | XX | 0.0014 | 0.056 |

Reactivity of Strained Cycloalkynes with Benzyl Azide:

The reactivity of the novel strained alkyne derivatives disclosed herein were first assessed using benzyl azide 5 as a model substrate (Table 1, model reaction at top). In acetonitrile at ambient temperatures, the second order rate constant for substrate 4b ($C_5H_{11}$) was found to be $2.5 \times 10^{-2}$ $M^{-1}$ $s^{-1}$. When steric hindrance was increased by placing the more bulky isopropyl group at C1, the rate of the reaction slowed to a sixth of that of substrate 4c. Conversely, decreasing the steric bulk in substrate 4a ($R^1$=Me) showed dramatically increased rate—the reaction proceeds 2.6 times faster than alkyne 4b. The effects of the heteroatoms in the ring were similarly pronounced. When the propargyl nitrogen was protected with a Boc group, the rate slowed slightly (4e). For Me-substituted substrates 4a and 4d, the rates slowed to roughly half their unprotected values. While a more electron-poor nitrogen heteroatom is expected to result in a stronger electronic effect and an expected increase in reaction rate, the conflicting effects of bond lengthening and steric repulsion between the Boc and $R^1$ groups overrides any benefit and results in a net slowing of rate. Similarly, when the homopropargylic oxygen atom was replaced with a Boc-protected nitrogen atom, the rate fell dramatically to an eighteenth of that of the sulfamate (4f). The fastest substrate, 1a, compares favorably to other reported strained alkynes. It is faster than OCT, the exocyclic heteroatom-activated MOFO, and the endocyclic heteroatom-activated alkynes reported by Toomoka et al., supra. The reaction rate of 1a is surpassed only slightly by DIFO. See Table 2 for comparison.

TABLE 2

Rate comparisions of common cycloalkynes with diazoazetamide and azidoacetamide in $CD_3CN$ ([a]$CD_3CN:D_2O$ = 1:1)

| | | |
|---|---|---|
| BCN | DIBONE | |
| $K_2$(7:8): 0.73 | 2.1 | |
| | DIBAC | 4a, R = H: 3.0, 8.5[a] |
| | 2.0, 6.5[a] | 4d, R = Boc: 5.0 |

Thus, the novel cyclooctynes described herein are sufficiently reactive for a large number of "click chemistry" applications. Furthermore, the inventive cyclooctynes are afforded in far fewer steps and higher yields than DIFO, providing for a much more accessible "click" reagent.

Designing Cyclooctynes with Increased Chemoselectivity:

Previous work directed towards the reactions of cyclooctynes has focused heavily on azide-alkyne cycloadditions. (See the above-noted references.) While this has been a fruitful area with many useful applications, cycloalkynes will partner with other substrates. Nitrones, nitrile oxides, and diazo compounds have all been demonstrated to undergo rapid reactions with strained alkynes without the need for transition metal catalysts. By looking beyond azides for coupling partners, new orthogonal labeling systems are accessible for providing tandem chemoselective transformations in a cellular context.

For these exploratory studies, diazoacetamide 8 (Table 3) and azidoacetamide 7 were chosen because of the increased nucleophilicity of 8 as compared to azide 7 andits ability to survive cellular metabolism. When comparing rate differences with diazoacetamide 8 and azidoacetamide 7 for common cycloalkynes, DIBAC reacted ~5-times faster with the diazoacetamide than the analogous azide in 1:1 $CD_3CN$: $D_2O$. This rate difference shows promise that the right balance of strain and electronic activation can be reached to provide for robust reagents displaying relatively rapid reaction kinetics. At the same time, these compounds provide for complete selectivity that is as of yet lacking in cyclooctynes. It was hypothesized by the present inventors that properly positioned heteroatoms in sulfamate-derived cyclooctynes would lead to an increase in diazo-selective reactivity over azides, thus enabling orthogonal bioconjugation techniques. It was found that under the same reaction conditions, the gap in reactivity for cycloalkyne 4 was even larger than that of DIBAC.

TABLE 3

Experimental rate constants and calculated activation energies and free energies (kcal/mol) for the lowest energy transition states for cycloadditions of diazo- and azidoacetamide reacting with alkynes 4a and 4d. Geometries were optimized at the M06-2X/6-311 + G(d, p) level of theory using an IEFPCM solvent model for water (radii = UFF). Bn was replaced with Me for simplicity in computations.

TABLE 3-continued

| | azidoacetamide, 7 | | | diazoacetamide, 8 | | |
|---|---|---|---|---|---|---|
| | $\Delta E^{\ddagger}_{calc.}$ (kcal/mol) | $\Delta G^{\ddagger}_{calc.}$ | $k_2$ (M$^{-1}$s$^{-1}$) | $\Delta E^{\ddagger}_{calc.}$ (kcal/mol) | $\Delta G^{\ddagger}_{calc.}$ | $k_2$ (M$^{-1}$s$^{-1}$) |
| 4a, R' = H | 11.5 | 23.8 | xx | 10.7 | 21.9 | xx |
| 4d, R' = Boc | 10.6 | 24.1 | xx | 10.1 | 23.1 | xx |

The effects of the various heteroatoms on this increased chemoselectivity were investigated computationally. Reaction of the standard substrate 4 (Table 3) with diazoacetamide 8 was found experimentally to be about an order of magnitude faster than reaction with azidoacetamide 7. This observation suggests a $\Delta\Delta G^{\ddagger}$ of ~1.3 kcal/mol, while computations predicted $\Delta\Delta G^{\ddagger}$ and $\Delta\Delta E^{\ddagger}$ values of 1.9 and 0.8 kcal/mol, respectively, for the unsubstituted sulfamates 4a. Computations indicated that Boc-substitution decreases the $\Delta\Delta E^{\ddagger}$ for reaction of both the diazoacetamide and azidoacetimide as the nitrogen becomes a better σ-acceptor. In contrast, the $\Delta\Delta G^{\ddagger}$ is expected to increase, likely due to increased steric repulsion from the bulky Boc-group. This difference in rate provides ~9:1 selectivity in competition experiments involving 1:1:1 mixtures of diazoacetamide (7):azidoacetamide (8):alkyne (4d, 4e). Efforts to improve the selectivity for reaction with 1 were undertaken by examining the effects of both propargylic and homopropargylic heteroatoms in 4.

Figure 1:
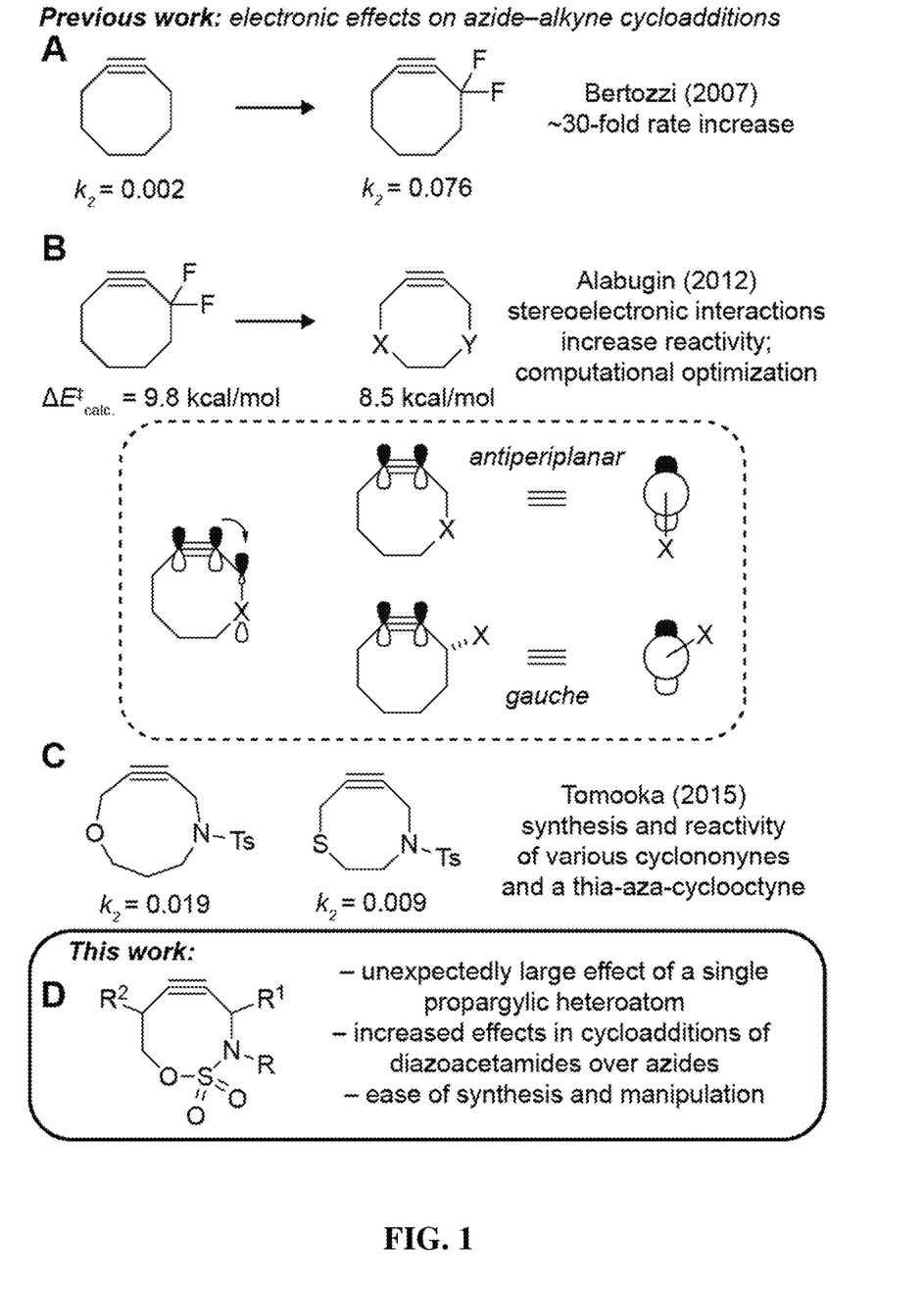
FIG. 1 is a series of illustrations depicting various types of prior art SPAAC-type reactions (panels A, B, and C) as contrasted to the present process (panel D). Panels A, B, and C note the electronic effects on rate and selectivity of the various types of strain-promoted 1,3-dipolar-alkyne cycloadditions.

In the most closely related system, the cyclooctyne previously reported by Toomoka (FIG. 1, panel C), an N-tosyl and thioether linker occupy each of the endocyclic propargylic sites. The compounds and methods disclosed herein differ in two key ways. First, only one of the endocyclic propargylic positions is occupied by a heteroatom (nitrogen; see FIG. 1, panel D) and second, the nature of the endocyclic sulfamate replaces two carbon atoms of the ring with heteroatoms (oxygen and sulfur). Based on these features, it is reasonable to expect slower rates with compounds according to the present invention (such as 4; see Table 1) as compared to Toomoka's alkyne as shown in FIG. 1, panel C. This is because the inventive compounds experience hyperconjugative assistance from only one propargylic heteroatom. However, that's not the case. Experimental results showed enhanced reactivity of the present compounds as compared to Toomoka's. This was a very surprising and unexpected outcome.

Computational Studies of Cycloalkynes:

Introduction of a sulfonyl group into an all-carbon cyclooctyne ring relieves ring strain as a result of long C—S bonds and an increase in the linearization of alkyne angles (~158/159° to ~161/161°). In addition, the homopropargylic sulfonyl generates a more polar transition state in a cycloaddition reaction, as determined by NBO charges on the reacting partners. (Data not shown.) This is due to inductive effects, as well as double hyperconjugation through the exocyclic propargylic C—C bonds. This renders the $\Delta\Delta G^{\ddagger}$ upon sulfonyl incorporation (4i) smaller for the diazoacetamide than for the azide. However, the way in which the two heteroatoms adjacent to the sulfonyl group (N and O in the case of the sulfamate of 4a) interact synergistically to increase the reactivity of the inventive cycloalkynes was not clear. To address this issue, computational studies were undertaken.

Figure 2:
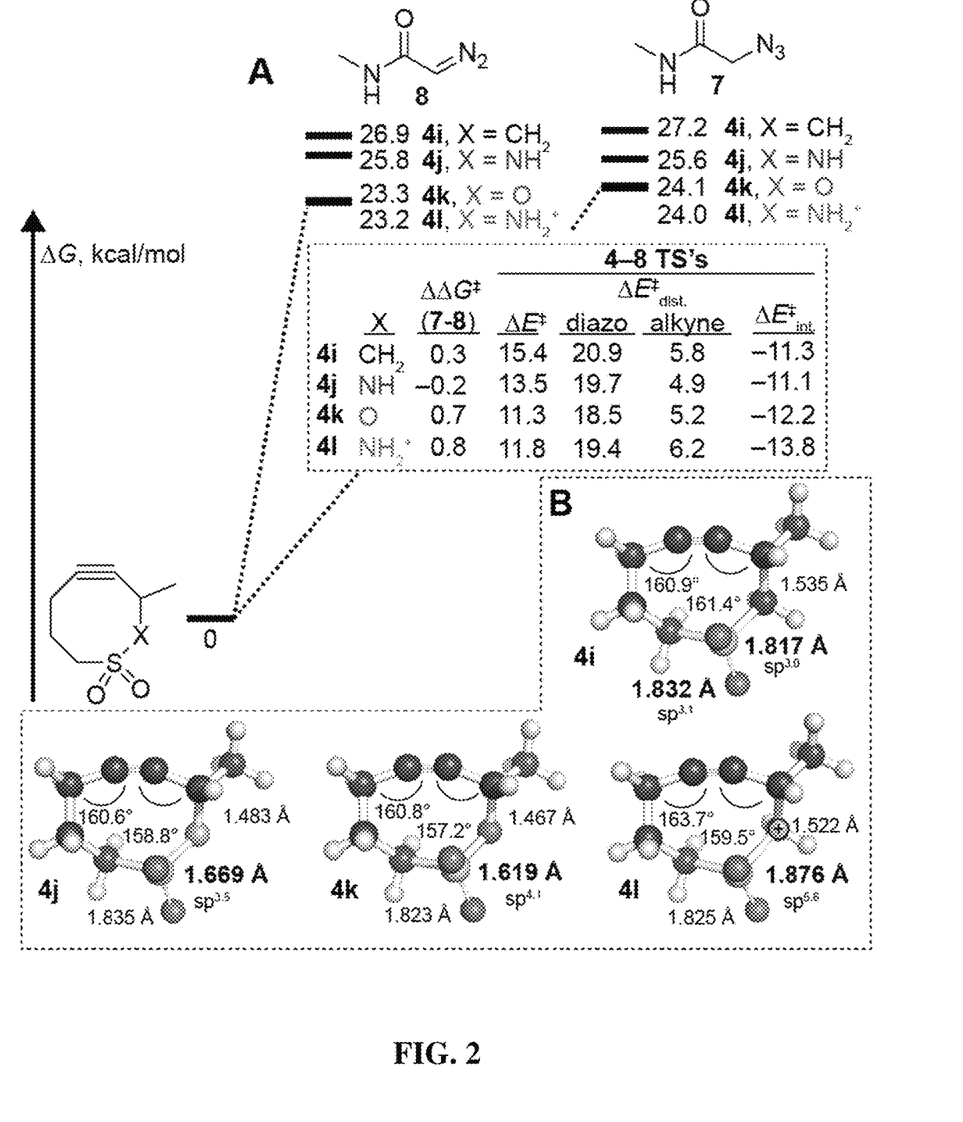
FIG. 2 is an illustration depicting, in panel A, the free energies of activation (kcal/mol) of the lowest energy transition states for each cycloadditionsof diazo- and azidoacetamides reacting with alkynes containing various propargylic substituents. Geometries optimized at the M06-2X/6-311+G(d,p) level of theory with an IEFPCM solvent model for water (radii=UFF). Inset: Distortion/interaction analysis for cycloadditions of diazoacetamide. Panel B depicts starting alkyne geometries with selected bond lengths given in Å and angles in degrees. Hybridizations obtained from NBO analysis are given for sulfur bonding orbitals in S—X bonds. Black=carbon; white=hydrogen; blue=nitrogen; red=oxygen; yellow=sulfur.

Both the observed chemo- and regioselectivity were recapitulated by calculated values, where both dipoles favored approaching "anti" to the propargylic nitrogen and methyl group. To assess the effect of the sulfonyl group on previously reported π→σ* C—X interactions, a series of compounds differing in the electron-accepting ability of the propargylic σ bond were examined (X=NH, O, NH$_2^+$; see FIG. 2, panel A). All three heteroatoms decrease the barrier relative to compound 4i, containing only an SO$_2$ group. Additionally, increased selectivity for cycloadditions of the diazoacetamide is predicted (larger $\Delta\Delta G^{\ddagger}$ values) for compounds 4k and 4l (X=O and NH$_2^+$, respectively).

Decreased activation energies were expected as the electron-acceptor abilities of the X group were increased, but this trend was not followed. The reaction of diazoacetamide 8 and 4k displayed a lower activation energy (and a nearly identical free energy of activation) than the reaction with 4l (see FIG. 2). Without being constrained to a given mechanism, this is thought to result from an increased S—N bond length upon protonation of the nitrogen, a direct effect of Bent's rule. (Bent, H. A. (1961) "An appraisal of valence-bond structures and hybridization in compounds of the first-row elements," *Chem. Rev.* 61(3):275-311.) As the electronegativity of the propargylic atom is increased, the sulfur utilizes more p-character in the bonding orbital directed towards atom X, amounting to an increase from sp$^{3.5}$ to sp$^{4.1}$ to sp$^{5.6}$ for compounds 4j-l (NH, O, and NH$_2^+$, respectively; hybridization values obtained from NBO analysis). This results in calculated S—X bond lengths of 1.67 Å, 1.62 Å and 1.88 Å for the same series, compared to the S—C length of 1.82 Å for compound 4j. In addition to changes in hybridization, anomeric effects also influence the S—X bond length. The endo-anomeric effect (nX→σ*$_{S-Y}$ and nXσ*$_{S=O}$) induces double bond character between the S and X, while the exo-anomeric effect (nO→σ*$_{S-X}$) lengthens the S—X bond. Thus, in the case of X=NH$_2^+$, the exo-anomeric effect is strengthened and there is no longer a lone pair to engage in the endo-anomeric effect.

More importantly, the reactivity of the alkyne is affected by both the acceptor ability of the propargylic heteroatom and the ring strain, where the angle at the proximal alkyne carbon increases from 157.2° to 158.80 to 159.50 for compounds 4k, 4j, and 4l (O, NH, and $NH_2^+$, respectively). All of these derivatives display increased bending relative to the ~161° of compound 4i, but the lengthening of the S—N bond due to protonation outweighs the increased acceptor abilities in compound 4l. These findings are recapitulated by the distortion/interaction analysis (vide infra). In summary, the bond length, dictated by the identity of the heteroatom at the X position, has a substantial effect on the reactivity of the molecule, with the shortest bond lengths and relatively high electronegativity associated with propargylic oxygen atoms giving the highest reactivity. While electronic tuning via substitution at the propargylic nitrogen may provide for increased reactivity, the delicate balance of increased electronegativity competing with structural relaxation renders the free NH the most reactive of analogs which have been synthesized to date.

The effects of the homopropargylic heteroatom Y in 4 were investigated in a fashion similar to that described above for X. The substituents in the Y position were modified and X was fixed as a methylene group. The effects were surprisingly large, with over a 2 kcal/mol decrease in $\Delta E^\ddagger$ and $\Delta G^\ddagger$ noted. For the heteroatoms utilized experimentally (X=NH, Y=O), the effect of the homopropargylic oxygen in 4n is larger than that of the propargylic nitrogen in 4j. The increased reactivity as a result of homopropargylic heteroatoms stems from a slight increase in electrophilicity via inductive effects and also double hyperconjugation through exocyclic propargylic C—H bonds. These effects are moderated, however, by bond length alterations according to Bent's rule, as discussed above. This marks the first description of the participation of an endocyclic heteroatom at the homopropargylic positions in the reactivity of the strained alkyne.

Figure 3:
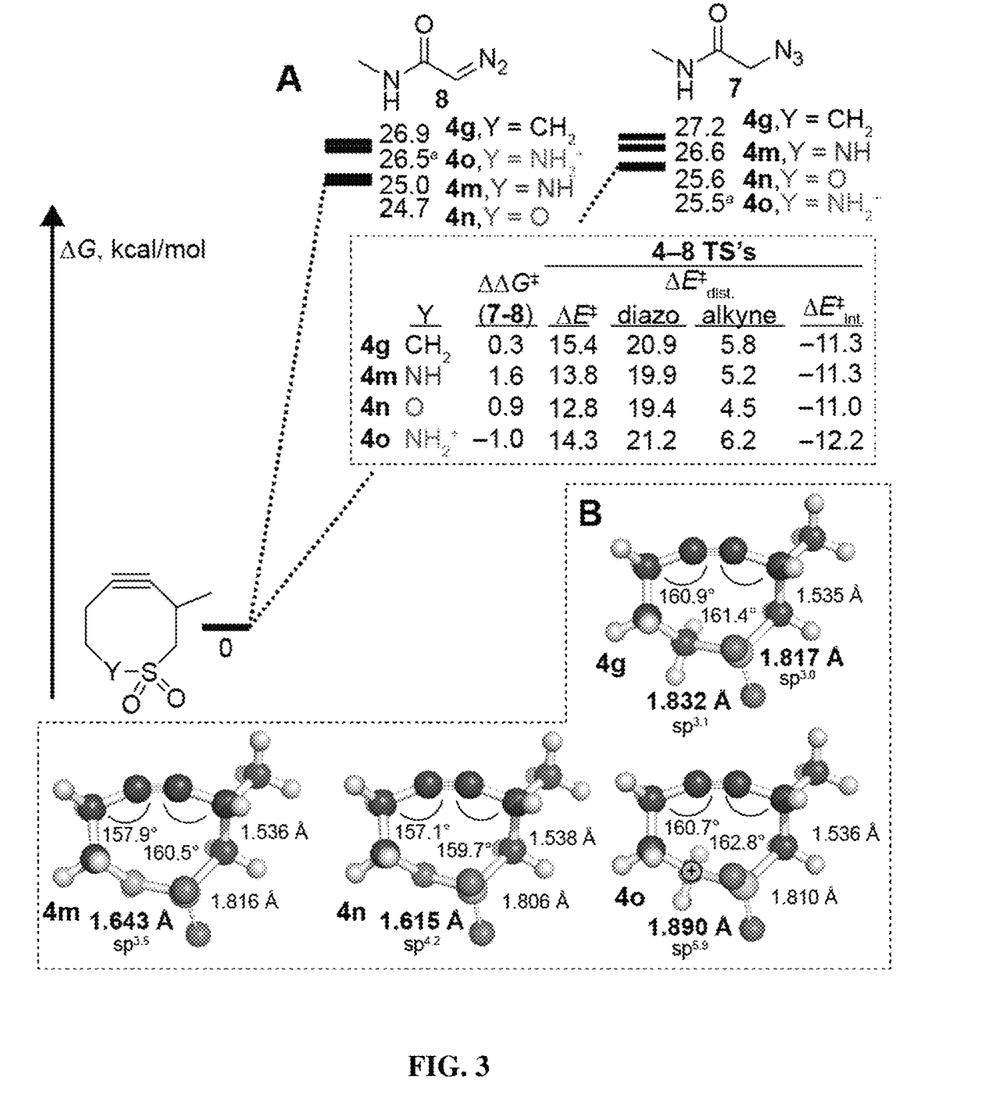
FIG. 3 is an illustration depicting, in panel A, the free energies of activation (kcal/mol) of the lowest energy transition states for each cycloadditions of diazo- and azidoacetamides reacting with alkynes containing various homopropargylic substituents. Geometries optimized at the M06-2X/6-311+G(d,p) level of theory with an IEFPCM solvent model for water (radii=UFF). Inset: Distortion/interaction analysis for cycloadditions of diazoacetamide. Panel B depicts the starting alkyne geometries with selected bond lengths given in Å and angles in degrees. Hybridizations obtained from NBO analysis given for sulfur bonding orbitals in S—Y bonds. Black=carbon; white=hydrogen; blue=nitrogen; red=oxygen; yellow=sulfur. [a]Syn transition state is preferred.

Finally, the combination of the effects of both X and Y in 4 were explored. See FIG. 3. In many cases, synergistic effects of the propargylic and homopropargylic heteroatom were observed, resulting in increased reactivity when reacted with a standard alkyl azide 7 or diazoacetamide 8. As the ultimate goal was to simultaneously enhance both reactivity and selectivity, there was an interest in cases with improved reactivity where the $\Delta\Delta G^\ddagger$ between the dipoles is also increased. Interestingly, this holds true in compounds 4w and 4v (X=$NH_2^+$ and Y=O or $NH_2^+$). In this situation, where there is no heteroatom at the Y position, favorable electronics were outweighed by unfavorable geometric relaxation. The sulfur atom must accommodate electronegative substituents at both the X and Y position, preventing the high p-character and bond lengthening in either of the two bonding orbitals (FIG. 3). This allows for both the large interactions provided by a highly electronegative propargylic heteroatom, without the counterproductive bond lengthening as a result of Bent's rule. This effect is readily apparent in compound 4s (X=Y=O), where the alkyne is bent to a significant degree as a result of significantly shortened S—X and S—Y bond lengths (<1.6 Ångstroms). Previous reports of decreased reactivity upon thioether incorporation are overcome when the endocyclic sulfur atom must accommodate multiple electronegative atoms simultaneously. This provides a unique opportunity to alter alkyne distortion/strain electronically, rather than through the incorporation of annealed rings or additional $sp^2$ centers.

Figure 4:
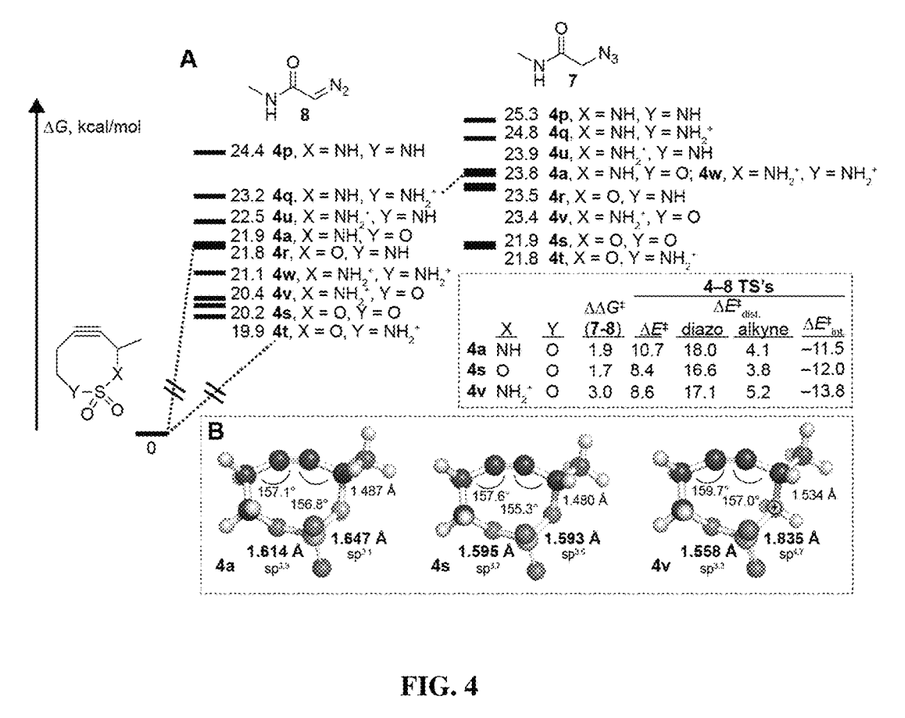
FIG. 4 is an illustration depicting, in panel A, the free energies of activation (kcal/mol) of the lowest energy transition states for each cycloadditions of diazo- and azidoacetamides reacting with alkynes containing various propargylic and homopropargylic substituents. Geometries optimized at the M06-2X/6-311+G(d,p) level of theory with an IEFPCM solvent model for water (radii=UFF). Inset: Distortion/interaction analysis for selected cycloadditions of diazoacetamide. Panel B depicts the starting alkyne geometries with selected bond lengths given in Ång-stroms and angles in degrees. Hybridizations obtained from NBO analysis given for sulfur bonding orbitals in S—X and S—Y bonds. Black=carbon; white=hydrogen; blue=nitrogen; red=oxygen; yellow=sulfur.
Figure 5:
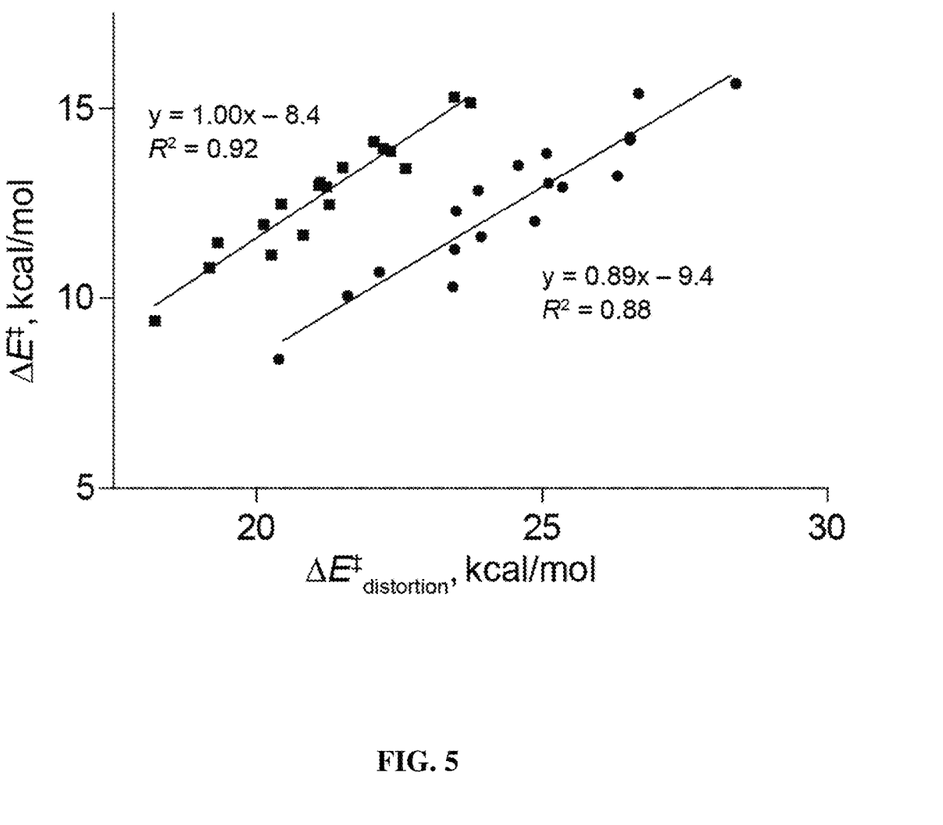
FIG. 5 is a series of superimposed plots of activation energies versus distortion energies split by the diazoacetamide (circles) and azidoacetamide (squares) for all cycloadditions evaluated to date, excluding charged alkynes.

Distortion/interaction (analogously termed strain activation) analysis was employed to elucidate structural effects on the reactivity of 4 when the identity of X and Y are varied (FIGS. 3, 4, and 5). In cases of a single heteroatom in either the X or Y position, the relatively short S—NH and S—O bonds, compared to S—C and S—$NH_2^+$, give decreased alkyne distortion energies (FIGS. 3 and 4). Due to increased S—$NH_2^+$ bond lengths, increased distortion energies are observed, however, large interactions partially compensate for the increased distortion energy.

When effects are combined and heteroatoms are placed at both the X and Y positions, the major effect is a decrease in the distortion energy rather than an increase in interactions. Charged species benefit from both a decrease in distortion energies and an increase in interaction energies—as a second heteroatom mediates the bond lengthening due to changes in hybridization—giving extremely low energies of activation.

While the distortion/interaction analysis accurately describes reactivity trends of each dipole with various alkynes (minus charged species that benefit from large interactions, FIG. 4), the analysis breaks down when plotting reactions of azide X and diazoacetamide Y together. This is due to the fact that stabilized diazoacetamides display artificially high distortion energies that are compensated for by increased interaction energies. Conjugative stabilization in the starting material is traded for bond formation, simultaneously increasing both distortion and interaction energies.

As a result of increased hyperconjugative interactions in the transition state, large interactions are observed for both X=O and $NH_2^+$. In the case of X=O, favorable interaction energies are accompanied by a decrease in distortion— previously described as assistance to alkyne bending accompanied by assistance to bond formation. In the case of X (and Y)=$NH_2^+$, however, the favorable interactions are negated by the increased distortion energies resulting from the geometric relaxation of the alkyne. As a result, inclusion of charged species into plots of activation energies against total distortion energies provides for very low correlation. When charged alkynes are removed, good correlation is observed, especially when each regioisomer is plotted independently.

In conclusion, disclosed herein are cyclooctynes bearing endocyclic heteroatoms that are able to tune alkyne electronics for varying degrees of reactivity amongst various 1,3-dipoles. Increased rates, high stability, and ease of synthesis relative to previously reported systems makes for an attractive compound for a number of applications.

The electronic nature of azido and diazo dipoles render this an ideal system for chemo- and regioselectivity in noncatalyzed 1,3-dipolar cycloadditions activated by strain. The current system allows for complete regioselectivity in reactions with diazoacetamides and the highest chemoselectivity reported between the diazo-acetamide and the analogous azide reacting with a cyclooctyne to date.

We have also unveiled a new method for the attenuation of strain in starting cycloalkynes. An interplay of anomeric effects and bond lengths dictated by hybridization is be predictably controlled by the choice of endocyclic heteroatoms.

What is claimed is:

1. Compounds of Formula I:

(Formula I)

wherein:
$R^1$ and $R^2$ are independently selected from hydrogen and $C_1$ to $C_{12}$ linear or branched alkyl;
$R^3$ is selected from hydrogen, $C_1$ to $C_{12}$ linear or branched alkyl, and nitrogen protecting groups;
X is oxygen or nitrogen;
when X is oxygen, $R^4$ is absent; and
when X is nitrogen, $R^4$ is selected from $C_1$ to $C_{12}$ linear or branched alkyl and nitrogen protecting groups.

2. The compounds of claim 1, wherein X is oxygen.
3. The compounds of claim 1, wherein X is nitrogen.
4. The compounds of claim 3, wherein $R^4$ is $C_1$ to $C_{12}$ linear or branched alkyl.
5. The compounds of claim 3, wherein $R^4$ a nitrogen protecting group.
6. A compound of claim 1, wherein one of $R^1$ or $R^2$ is $C_1$ to $C_{12}$ linear or branched alkyl.
7. The compounds of claim 6, wherein X is oxygen.
8. The compounds of claim 6, wherein X is nitrogen.
9. The compounds of claim 8, wherein $R^4$ is $C_1$ to $C_{12}$ linear or branched alkyl.
10. The compounds of claim 8, wherein $R^4$ a nitrogen protecting group.
11. A compound of claim 1, wherein $R^1$ and $R^2$ are $C_1$ to $C_{12}$ linear or branched alkyl.
12. The compounds of claim 11, wherein X is oxygen.
13. The compounds of claim 11, wherein X is nitrogen.
14. The compounds of claim 13, wherein $R^4$ is $C_1$ to $C_{12}$ linear or branched alkyl.
15. The compounds of claim 13, wherein $R^4$ a nitrogen protecting group.
16. A compound of claim 1, wherein one of $R^1$ or $R^2$ is $C_1$ to $C_6$ linear or branched alkyl.
17. The compounds of claim 16, wherein X is oxygen.
18. The compounds of claim 16, wherein X is nitrogen.
19. The compounds of claim 18, wherein $R^4$ is $C_1$ to $C_{12}$ linear or branched alkyl.
20. The compounds of claim 18, wherein $R^4$ a nitrogen protecting group.
21. A compound of claim 1, wherein $R^1$ and $R^2$ are $C_1$ to $C_6$ linear or branched alkyl.
22. The compounds of claim 21, wherein X is oxygen.
23. The compounds of claim 21, wherein X is nitrogen.
24. The compounds of claim 23, wherein $R^4$ is $C_1$ to $C_{12}$ linear or branched alkyl.
25. The compounds of claim 23, wherein $R^4$ a nitrogen protecting group.
26. A method of forming chemical bonds, the method comprising reacting a first compound of Formula I:

(Formula I)

wherein:
$R^1$ and $R^2$ are independently selected from hydrogen and $C_1$ to $C_{12}$ linear or branched alkyl;
$R^3$ is selected from hydrogen, $C_1$ to $C_{12}$ linear or branched alkyl, and nitrogen protecting groups;
X is oxygen or nitrogen;
when X is oxygen, $R^4$ is absent; and
when X is nitrogen, $R^4$ is selected from $C_1$ to $C_{12}$ linear or branched alkyl and nitrogen protecting groups;
with a second compound comprising a 1,3-dipole, in a 1,3-cycloaddition reaction.

* * * * *